United States Patent [19]

Purcell et al.

[11] Patent Number: 5,198,009
[45] Date of Patent: Mar. 30, 1993

[54] METHOD OF MANUFACTURING GLASS BEADS FOR USE IN THERMIONIC GAS CHROMATOGRAPHIC DETECTORS

[75] Inventors: John E. Purcell, New Milford; Richard Dang, Stamford, both of Conn.

[73] Assignee: The Perkin Elmer Corporation, Norwalk, Conn.

[21] Appl. No.: 796,497

[22] Filed: Nov. 22, 1991

[51] Int. Cl.⁵ .......................................... C03C 27/02
[52] U.S. Cl. .................... 65/59.220; 29/838; 29/841; 29/850; 29/859; 65/59.35; 65/21.3; 65/59.6; 65/139
[58] Field of Search ............ 65/21.1, 21.3, 59.25, 65/59.2, 59.22, 59.31, 59.35, 59.6, 139, 50; 29/613, 838, 841, 850, 855, 859, 862, 866

[56] References Cited

U.S. PATENT DOCUMENTS

| | | | |
|---|---|---|---|
| 3,226,218 | 12/1965 | Belkamp | 65/139 |
| 3,269,819 | 8/1966 | Cropp et al. | 65/59.2 |
| 3,461,532 | 8/1969 | Lybarger | 65/139 X |
| 3,852,037 | 12/1974 | Kolb et al. | 23/254 EF |
| 4,203,726 | 5/1980 | Patterson | 23/232 F |

OTHER PUBLICATIONS

Burgett, Smith, Bente, Wirfel & Goodhart; Chromatographic Capabilities of the Nitrogen-Phosphorus Selective Detector; Hewlett-Packard, Avondale, Pa.
Hartigan, Purcell, Novotny, McConnell & Lee; Journal of Chromatography 99 (1974) 339-348.
Greenhalgh, Muller & Aue; Journal of Chromatographic Science, vol. 16, Jan. 1978.
ASTM Designation: E 1140-86.
Lubkowitz, Semonian, Galobardes & Rogers; Analytical Chemistry, vol. 50, No. 4, Apr. 1978.
Perkin-Elmer Order No. L-394, Sep. 1974.

*Primary Examiner*—Robert L. Lindsay
*Attorney, Agent, or Firm*—John R. Wahl; Edwin T. Grimes

[57] ABSTRACT

Alkali metal-containing glass beads for use as sources in thermionic detectors for gas chromatography are manufactured by a method which produces reproducible beads of preselected sizes. A glass tube of the desired composition is reduced to capillary size. A section having the volume of the desired bead is cut from the capillary tube and threaded onto a support wire. It is then melted and caused to coalesce onto the support wire. The resultant bead and a portion of the support wire are then incorporated into the detector.

14 Claims, 1 Drawing Sheet

METHOD OF MANUFACTURING GLASS BEADS FOR USE IN THERMIONIC GAS CHROMATOGRAPHIC DETECTORS

TECHNICAL FIELD

This invention relates to the field of gas chromatographic detectors. More specifically, it relates to the manufacture of alkali metal-containing glass beads for use as sources in such detectors.

BACKGROUND ART

It is well known to employ glass beads containing alkali metals as sources in thermionic gas chromatographic detectors. Detectors utilizing such beads are particularly useful as nitrogen and phosphorous detectors. Such a detector is disclosed in U.S. Pat. No. 3,852,037 of Kolb et al. which issued Dec. 3, 1974. Methods of manufacturing such beads are disclosed, inter alia, in an article by Greenhalgh, Müller, and Aue in 16 *Journal of Chromatographic Science* 8 of January 1978 and in an article by Lubkowitz, Semonian, Galobardes, and Rogers appearing in 50 *Analytical Chemistry* No. 4, 672, April 1978.

Particularly advantageous beads include rubidium or cesium-containing glass. Currently, such beads are produced heating the ends of two soda-lime glass rods to a molten state by means of a hydrogen-hydrocarbon torch flame. The molten rod ends are dipped into a rubidium powder. The rod ends are then remelted and touched together. The resultant rubidium-glass mixture is then pulled into fine fibers in the flame. Using the same flame, small pieces of these rubidium-glass fibers are then melted onto a platinum wire until, by trial and error, a bead of 1 mm ($\pm 0.1$ mm) diameter is obtained. Frequently during heating the platinum wire is overheated, droops, and is then straightened by pulling from both ends.

The rubidium-containing beads produced in this manner are subject to a high rejection rate. They are expensive, neither physically nor chemically uniform, and are short lived. Due to having been stressed during manufacture, the beads may have air voids and fractures and the platinum wire frequently breaks in use.

Accordingly, it is a primary object of the present invention to provide an improved method of manufacturing such beads. Another object is to provide such a method wherein the beads are more uniform, contain a preselected and known volume of material, and are more reproducible. Other objects, features and advantage will be apparent from the following description and appended claims.

DISCLOSURE OF INVENTION

In accordance with the present invention, a rubidium or cesium-containing glass tube is reduced to capillary dimensions by well-known heating and pulling techniques. A small piece of the tubing, having a volume corresponding to that of the desired bead, is then cut from the tube. This piece is threaded onto a platinum or rhodium/platinum alloy wire. Thereafter, the capillary glass section is melted onto the wire, either by sending an electrical current through the wire or by heating from an external source.

BEST MODE FOR CARRYING OUT THE INVENTION

Figure 1:
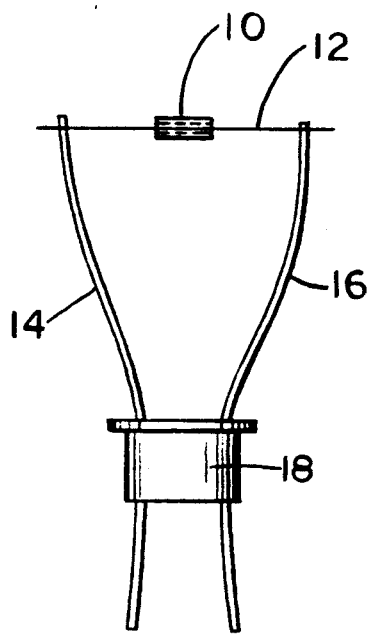
FIG. 1 is an elevational view of a fixture supporting a wire having a capillary tube section threaded thereon and positioned for manufacturing a bead.

A glass capillary tube having the desired composition and content of alkali metal is drawn to the appropriate dimension. It might have, for example, an internal diameter of 0.0085 inch (0.216 mm) and a wall thickness of 0.005 inch (0.127 mm). A small section having the desired glass volume is cut from the tube. The capillary tube section 10 is then threaded onto a length of support wire, such as platinum wire 12, which, in this example, might have a diameter of 0.007 inch (0.178 mm). The support wire 12 is then welded to an appropriate fixture which, as illustrated in FIG. 1, might comprise a pair of conductors 14, 16 held in an insulated spacer 18.

Figure 2:
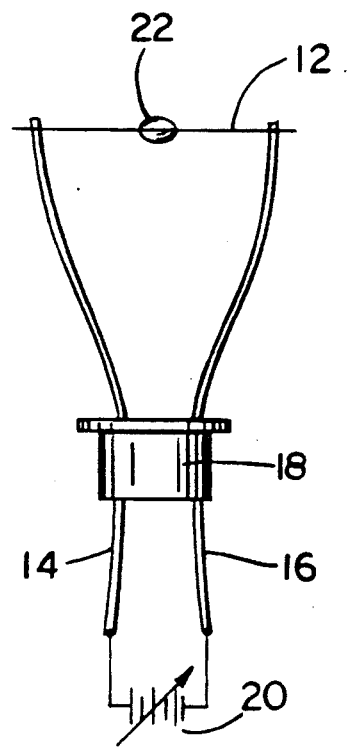
FIG. 2 is a view similar to that of FIG. 1, illustrating the succeeding step in the manufacture of the glass bead.

As illustrated in FIG. 2 the next step in the method of manufacturing the bead is to connect the ends of the conductors 14, 16 across a power supply 20. A DC current is then caused to flow through the support wire 12, causing the wire to heat and thereby melt the capillary tube section 10, causing it to coalesce into the desired bead 22. In the specific example referred to herein, a current of approximately 4 amperes will form the desired bead 22.

A bead actually formed in accordance with the foregoing example was ovoid in shape and had a length along the wire 12 of approximately $0.051 + 0.004$ inch ($1.3 \pm 0.1$ mm). Its transverse diameter was $0.036 \pm 0.004$ inch ($0.91 \pm 0.10$ mm).

Figure 3:
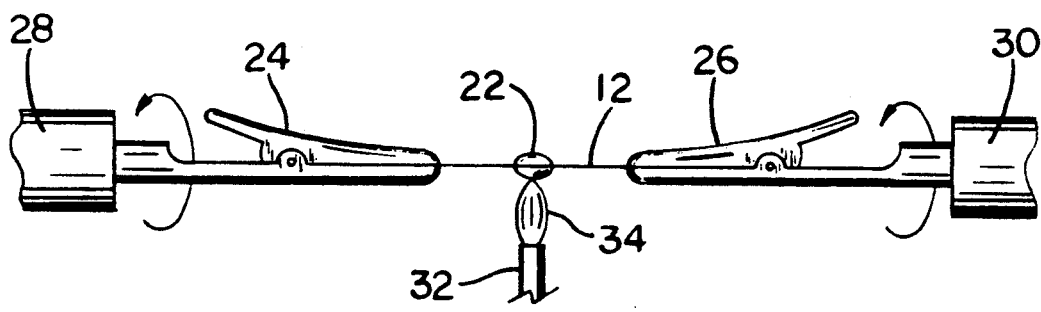
FIG. 3 is an elevational view illustrating a modified method for forming the glass bead.

A modification of the invention is illustrated in FIG. 3. In this modification, the capillary tube section is threaded upon the wire support 12 as previously explained. However, the wire 12 is then stretched between alligator clips 24, 26 which are mounted in the jaws 28, 30 of a modified lathe (not shown). The lathe is then rotated. A miniature propane-oxygen torch having a nozzle 32, which may be constructed from a hypodermic needle, produces a flame 34 which is then employed to heat the tube section to form the desired bead 22.

It will be understood by those skilled in the art that a number of variations and modifications may be made in this invention without departing from its spirit and scope. Accordingly, the foregoing description is to be construed as illustrative only, rather than limiting. This invention is limited only by the scope of the following claims.

We claim:

1. The method of manufacturing an alkali metal-containing bead for use as a detector source in gas chromatography which comprises:
   providing an electrically conductive support wire;
   providing a capillary tube formed of a glass containing said alkali metal in a preselected uniform desired concentration, said tube having an inside diameter capable of receiving said support wire therethroguh and having a glass volume substantially equivalent to that of the desired bead to be manufactured;

threading said tube onto said support wire; and melting said tube to form a substantially symmetrical bead having said preselected uniform concentration of alkali metal throughout the bead adhered to said support wire.

2. The method of claim 1 wherein said alkali metal is rubidium.

3. The method of claim 1 wherein said alkali metal is cesium.

4. The method of claim 1 wherein said support wire is a noble metal.

5. The method of claim 4 wherein said support wire is platinum.

6. The method of claim 4 wherein said support wire is a rhodium/platinum alloy.

7. The method of claim 5 wherein said alkali metal is rubidium.

8. The method of claim 1 wherein said tube is melted by passing an electrical current through said support wire.

9. The method of claim 1 wherein said tube is melted by subjecting it to an external heat source.

10. The method of claim 9 wherein said wire is rotated while subjecting said tube to the external heat source.

11. The method of claim 10 wherein said wire is tensioned so as to be substantially straight during rotation.

12. The method of claim 9 wherein said external heat source is a flame.

13. The method of claim 12 wherein said wire is rotated while subjecting said tube to the external heat source.

14. The method of claim 13 wherein said wire is tensioned so as to be substantially straight during rotation.

* * * * *